(12) United States Patent
Bottenus et al.

(10) Patent No.: US 11,583,254 B2
(45) Date of Patent: Feb. 21, 2023

(54) SYSTEMS AND METHODS FOR INTRA-BEAM COMPOUNDING FOR ULTRASOUND IMAGING

(71) Applicant: Duke University, Durham, NC (US)

(72) Inventors: Nicholas Bottenus, Durham, NC (US); Gregg Trahey, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/621,785

(22) PCT Filed: Jun. 28, 2018

(86) PCT No.: PCT/US2018/040015
§ 371 (c)(1),
(2) Date: Dec. 12, 2019

(87) PCT Pub. No.: WO2019/006124
PCT Pub. Date: Jan. 3, 2019

(65) Prior Publication Data
US 2021/0275149 A1    Sep. 9, 2021

Related U.S. Application Data

(60) Provisional application No. 62/525,980, filed on Jun. 28, 2017.

(51) Int. Cl.
*A61B 8/00*    (2006.01)
*A61B 8/08*    (2006.01)
(52) U.S. Cl.
CPC .......... *A61B 8/5207* (2013.01); *A61B 8/4488* (2013.01); *A61B 8/54* (2013.01)
(58) Field of Classification Search
CPC ........ A61B 8/54; A61B 8/4488; A61B 8/5207
See application file for complete search history.

(56) References Cited

U.S. PATENT DOCUMENTS 5,951,479 A    9/1999    Holm et al.
6,048,315 A *  4/2000    Chiao ................. G01S 15/8997
                                              600/447
(Continued)

FOREIGN PATENT DOCUMENTS

WO    2018/053084    3/2018
WO    2018/075721    4/2018

OTHER PUBLICATIONS

International Search Report and Written Opinion for PCT/US2018/040015 dated Sep. 19, 2018, 11 pages.
(Continued)

*Primary Examiner* — Christopher Koharski
*Assistant Examiner* — Taylor Deutsch
(74) *Attorney, Agent, or Firm* — Myers Bigel, P.A.

(57) ABSTRACT

A method for ultrasound imaging a target region including: (a) transmitting a tracking beam from at least a subset of the elements of the array to the region, each of the subset of the elements emitting a signal of the tracking beam with a respective transmission time shift; (b) receiving echo signals at at least some of the subset of the elements of the array, each echo signal being responsive to the tracking beam; (c) applying the time shift to at least some of the subset of the respective elements to the echo signals received at corresponding elements; (d) modifying the time shift and repeating (a)-(c) to provide an ultrasound dataset representing a recovered source element domain; (e) focusing and beamforming the dataset to map time signals of the dataset and combine channel signals to provide spatial pixel data; and (f) forming an ultrasound image from the spatial pixel data.

30 Claims, 12 Drawing Sheets

(56) References Cited

U.S. PATENT DOCUMENTS

| | | | |
|---|---|---|---|
| 6,050,947 A * | 4/2000 | Rhyne | A61B 8/481 600/447 |
| 6,231,511 B1 * | 5/2001 | Bae | G01S 7/52046 600/447 |
| 6,312,386 B1 | 11/2001 | Bolorforosh et al. | |
| 8,137,272 B2 | 3/2012 | Cooley et al. | |
| 8,317,712 B2 | 11/2012 | Burcher et al. | |
| 8,679,018 B2 | 3/2014 | Mclaughlin et al. | |
| 8,939,909 B2 | 1/2015 | Wegner | |
| 9,384,530 B2 | 7/2016 | Daigle | |
| 2009/0306512 A1 | 12/2009 | Loftman et al. | |
| 2014/0364737 A1 | 12/2014 | Huang et al. | |
| 2015/0265250 A1 | 9/2015 | Madore | |
| 2015/0297193 A1 * | 10/2015 | Rothberg | A61B 8/4483 600/459 |
| 2016/0061950 A1 | 3/2016 | Xu et al. | |

OTHER PUBLICATIONS

Bottenus, Nick, "A method for intrapulse spatial compounding", IEEE International Ultrasonics Symposium Proceedings, 2016, 4 pages.

Bottenus, Nick, "Comparision of virtual source synthetic aperture beamforming with an element-based model", J. Acoust. Soc. Am. 143 (5), May 2018, pp. 2801-2812.

Bottenus, Nick, "Recovery of the complete data set from ultrasound sequences with arbitrary transit delays," Proceedings on Meetings on Acoustics, vol. 31, 020001, 2018, 14 pages.

Bottenus, Nick, "Synthetic recovery of the complete harmonic data set," Proc. SPIE 10580, Medical Imaging 2018: Ultrasonic Imaging and Tomography, 105800D, Mar. 6, 2018, 10 pages.

Bottenus, Nick, "Recovery of the Complete Data Set From Focused Transmit Beams", IEEE Transactions on Ultrasonics, FerroElectrics, and Frequency Control, vol. 65, No. 1, Jan. 2018, pp. 30-38.

Bae, MH, et al., "A study of Synthetic-Aperture Imaging with Virtual Source Elements in B-Mode Ultrasound Imaging Systems", IEEE Transactions on Ultrasonics, Ferroelectrics and Frequency Control, vol. 47, No. 6, Nov. 2000, pp. 1510-1519.

* cited by examiner

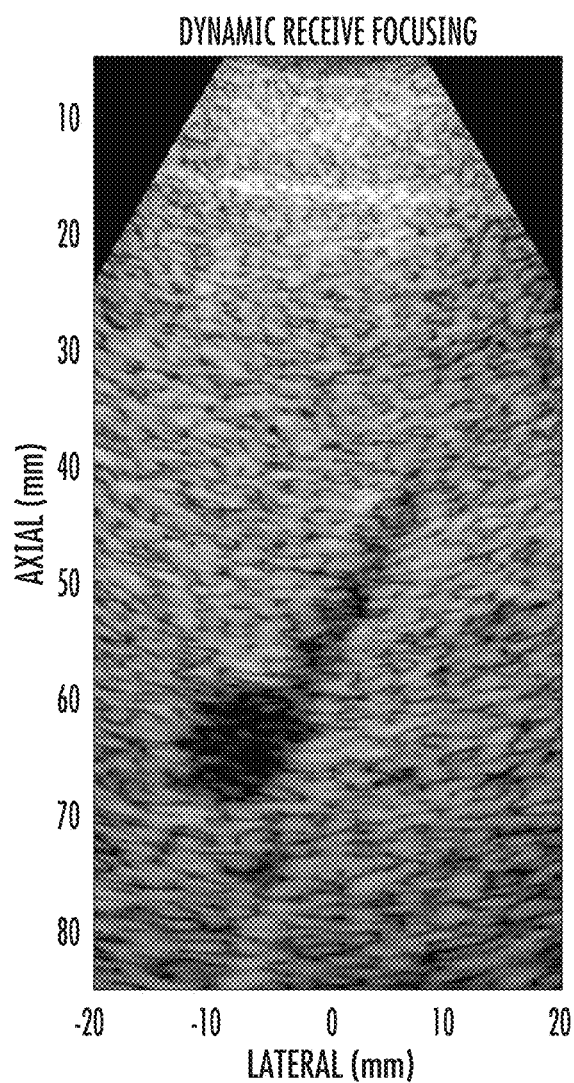 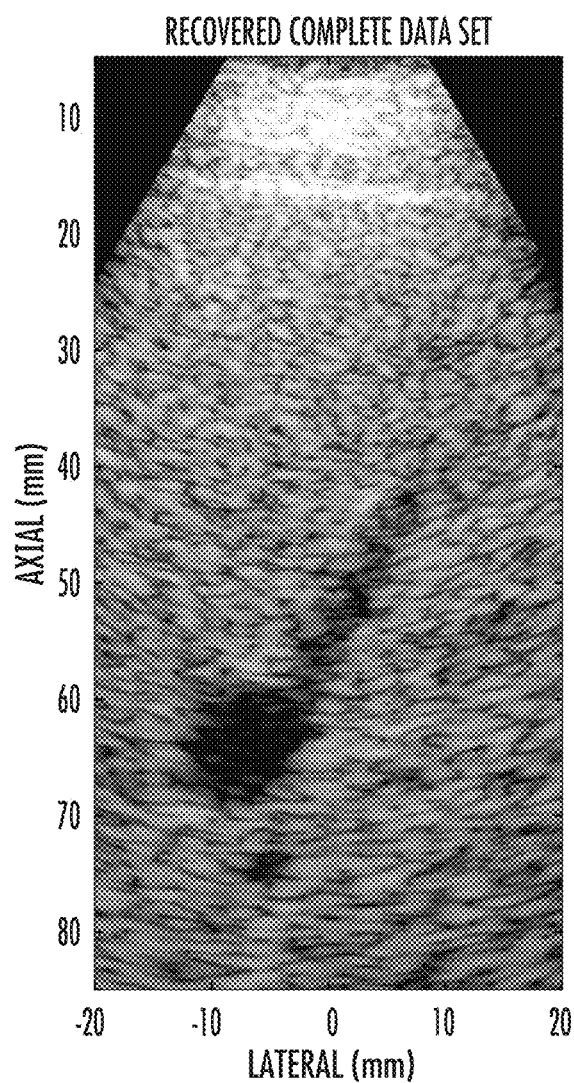
FIG. 7A (Prior Art)
FIG. 7B

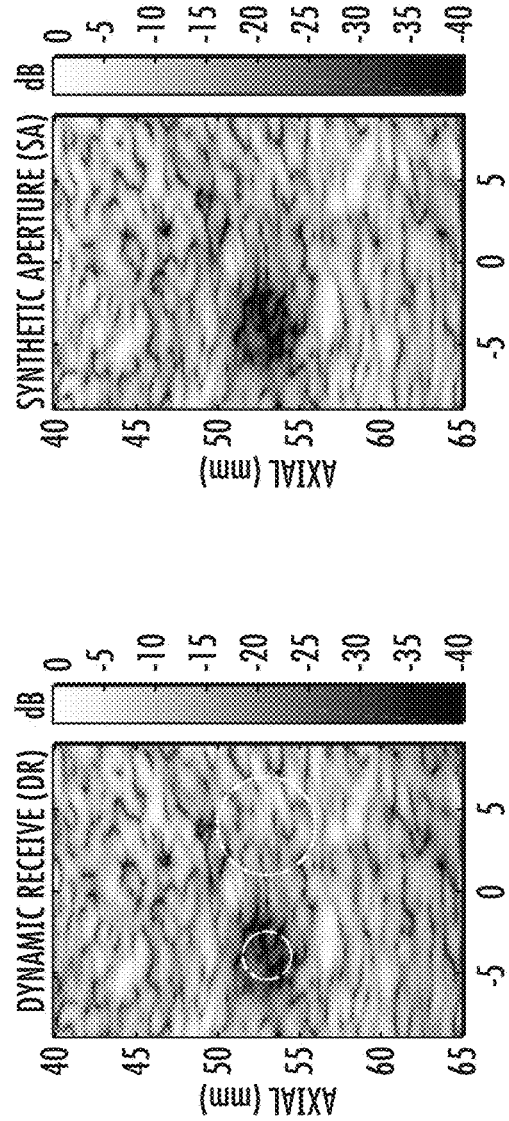
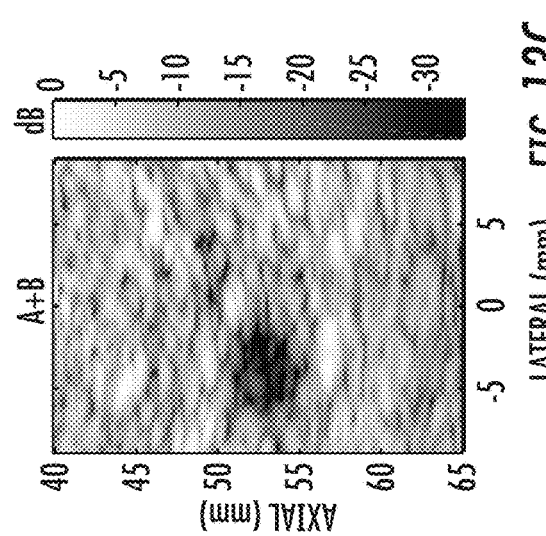
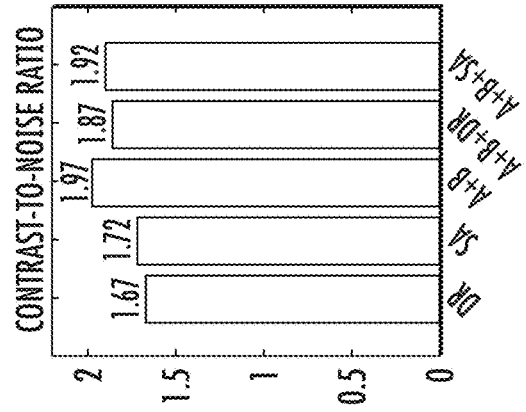
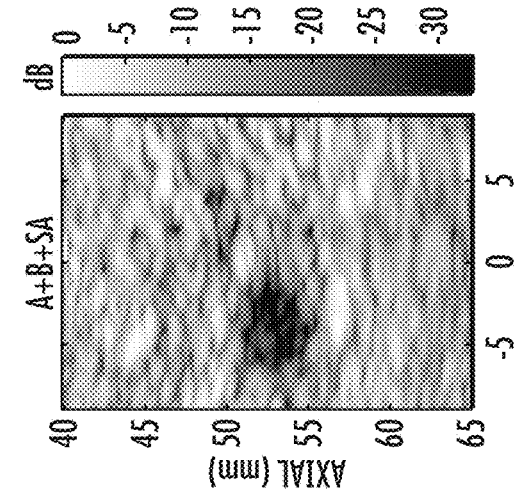
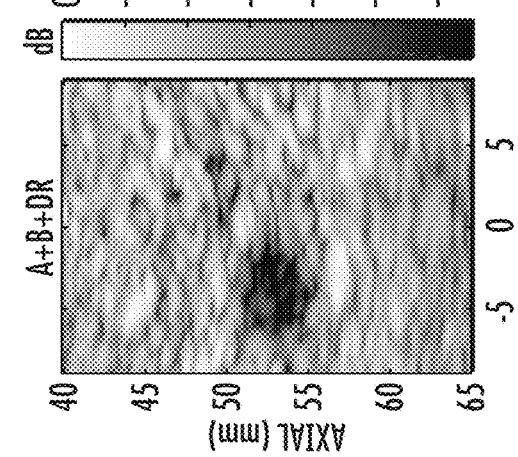

SYSTEMS AND METHODS FOR INTRA-BEAM COMPOUNDING FOR ULTRASOUND IMAGING

RELATED APPLICATIONS

This application is a 35 U.S.C. § 371 national stage application of PCT International Application No. PCT/US2018/040015, filed Jun. 28, 2018, which application claims priority to U.S. Provisional Application 62/525,980, filed Jun. 28, 2017, the disclosures of which are hereby incorporated by reference in their entireties.

FIELD OF THE INVENTION

The present invention relates to ultrasound imaging methods and systems.

BACKGROUND

Synthetic transmit aperture generally refers to collecting data from multiple transmit events representing varying aperture information (amplitude, phase, position, etc.) and coherently combining it using the appropriate geometric delays to create an augmented effective transmit aperture. U.S. Pat. No. 5,951,479 describes a fundamental implementation of this method, emitting on different segments of the array and creating the full array by coherent combination in post-processing.

U.S. Pat. No. 5,951,479 describes extending the focal depth of field by splitting the transmit aperture into inner and outer segments and using the segments independently to focus at different depths. This achieves better focusing across the axial extent of the image, but sacrifices SNR by splitting the active elements.

Synthetic transmit aperture techniques can be generalized to various beam geometries (focused, planar, diverging). U.S. Pat. No. 9,384,530 describes a method to determine the overlap between these shaped beams in order to determine where in the reconstruction to coherently combine them, creating a synthetic transmit aperture. U.S. Pat. No. 8,679,018B2 describes performing the technique with various broad beams.

The most common commercially implemented synthetic transmit aperture is similar to the method presented in U.S. Patent Application Publication No. 20090306512. For each focused beam, parallel receive lines are produced with varying delays to account for differences in transmit time of flight. The method uses the virtual source concept, with spherically converging waves propagating toward the focal point. Each receive point is created using contributions from a small set of neighboring steered beams that have been time and phase adjusted to align coherently. Similar methods are described in U.S. Pat. Nos. 6,231,511 and 8,137,272. U.S. Pat. No. 8,317,712 describes a similar method specifically for the application of spatial compounding.

U.S. Pat. No. 6,048,315 proposes a magnitude based coding (with values of +/−1) derived from the Hadamard matrix. This method allows for coherent combination of multiple transmit event data in order to recover individual channel data based on mathematical inversion of the Hadamard matrix. This method require accurate pulse inversion on transmit or reducing the number of elements emitting on each transmit (lowering signal-to-noise ratio) respectively.

SUMMARY OF EMBODIMENTS OF THE INVENTION

A method for ultrasound imaging a target region with an ultrasound system having an ultrasound transducer array with a plurality of ultrasound elements thereon includes: (a) transmitting an ultrasound tracking beam from at least a subset of the plurality of elements of the array to the target region, each of the subset of the plurality of elements emitting a signal of the tracking beam with a respective transmission time shift; (b) receiving a plurality of echo signals at at least of the subset of the plurality of elements of the array, each echo signal being responsive to the tracking pulse; (c) applying the transmission time shift to at at least some of the subset of the respective plurality of elements to the plurality of echo signals received at corresponding ones of the plurality of elements; (d) modifying the transmission time shift and repeating steps (a)-(c) to provide an ultrasound dataset representing a recovered source element domain of the ultrasound dataset; (e) focusing and beamforming the ultrasound dataset to map time signals of the ultrasound dataset and combine channel signals to provide spatial pixel data; and (f) forming an ultrasound image from the spatial pixel data.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 7A is an image of a vasculature from in vivo human liver produced with conventional dynamic receive focusing.

FIG. 7B is an image of a vasculature from in vivo human liver produced with recovery of the complete data set according to some embodiments.

FIGS. 13A-13E are images of in vivo liver tissue and vessel produced with various beamforming methods from the same focused transmit data set (129 beams, 50 mm focus) according to some embodiments. Detectability of the vessel at the focal depth compared to the speckle background as measured by the contrast-to-noise ratio improves by 18%.

FIG. 13F is a graph of the contrast to noise ratio of the images of FIGS. 13A-13E.

DETAILED DESCRIPTION OF EMBODIMENTS OF THE INVENTION

Figure 1:
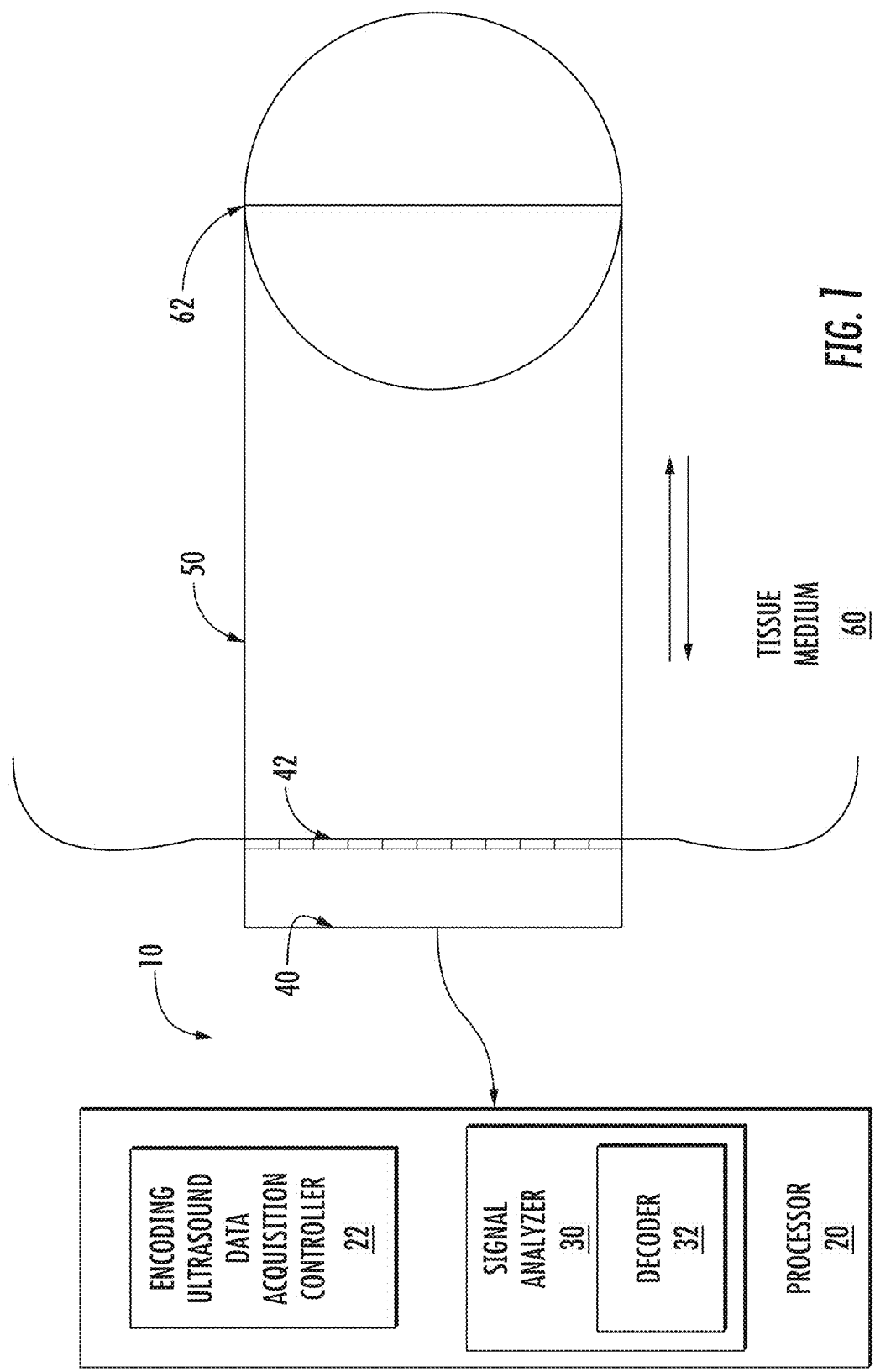
FIG. 1 is a schematic diagram of an ultrasound system and method according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention are described herein with reference to the term "tissue." It will be understood that the term tissue can include biological materials, such as, blood, organs, vessels, and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, two dimensional (2D) ultrasound imaging and 3D (or volumetric) ultrasound imaging. In addition, the components of the ultrasound imaging described herein may be packaged as a single unit or packaged separately and interconnected to provide the functions described herein.

As illustrated in FIG. 1, an ultrasound system 10 includes a processor 20 having a signal analyzer 30 and an ultrasound transducer array 40. The ultrasound transducer array 40 may include a plurality of array elements 42. The array elements 42 are configured to transmit and receive ultrasound signals 50, and may be contacted to a target medium such as a tissue medium 60. As illustrated, the tissue medium 60 includes a target region 62. As illustrated, the ultrasound array 40 may include ultrasound array elements 42 that define transmit/receive locations for transmitting and receiving ultrasound signals along a direction. The ultrasound transducer 40 may be configured to be controlled by the processor 20 and the controller 22 to transmit and detect ultrasound signals according to various types of ultrasound data, including B-mode imaging, harmonic imaging, ARFI imaging, SWEI imaging and the like. The ultrasound transducer array 40 may be a one-dimensional array configured to generate two-dimensional images or the ultrasound transducer array 40 may be a two-dimensional array configured to generate three-dimensional images.

The processor 20 may include an encoding ultrasound data acquisition controller 22 and the signal analyzer 30 may include a decoder 32 for analyzing the acquired data from the array 40. The encoding ultrasound data acquisition controller 22 and the signal analyzer 30 and decoder 32 may be configured to control the array 40 and/or to analyze echo signals received by the array 40 as described herein and may include hardware, such as control and/or analyzing circuits, and/or software stored on a non-transient computer readable medium for carrying out operations described herein.

As described herein, methods according to some embodiments modify a synthetic aperture focusing process, which achieves synthetic transmit focus by combining multiple emissions after accounting for their assumed times of flight to a selected point, to correspond to individual transmit elements. In some embodiments, an ultrasound method utilizes the focusing operation as a phase-based spatial encoding and performs efficient decoding either in the time or frequency domain before applying conventional beamforming, which may also provide an unfocused complete dataset. Both methods produce an equivalent output focused data set indexed by transmit element and receive channel.

Figure 2:
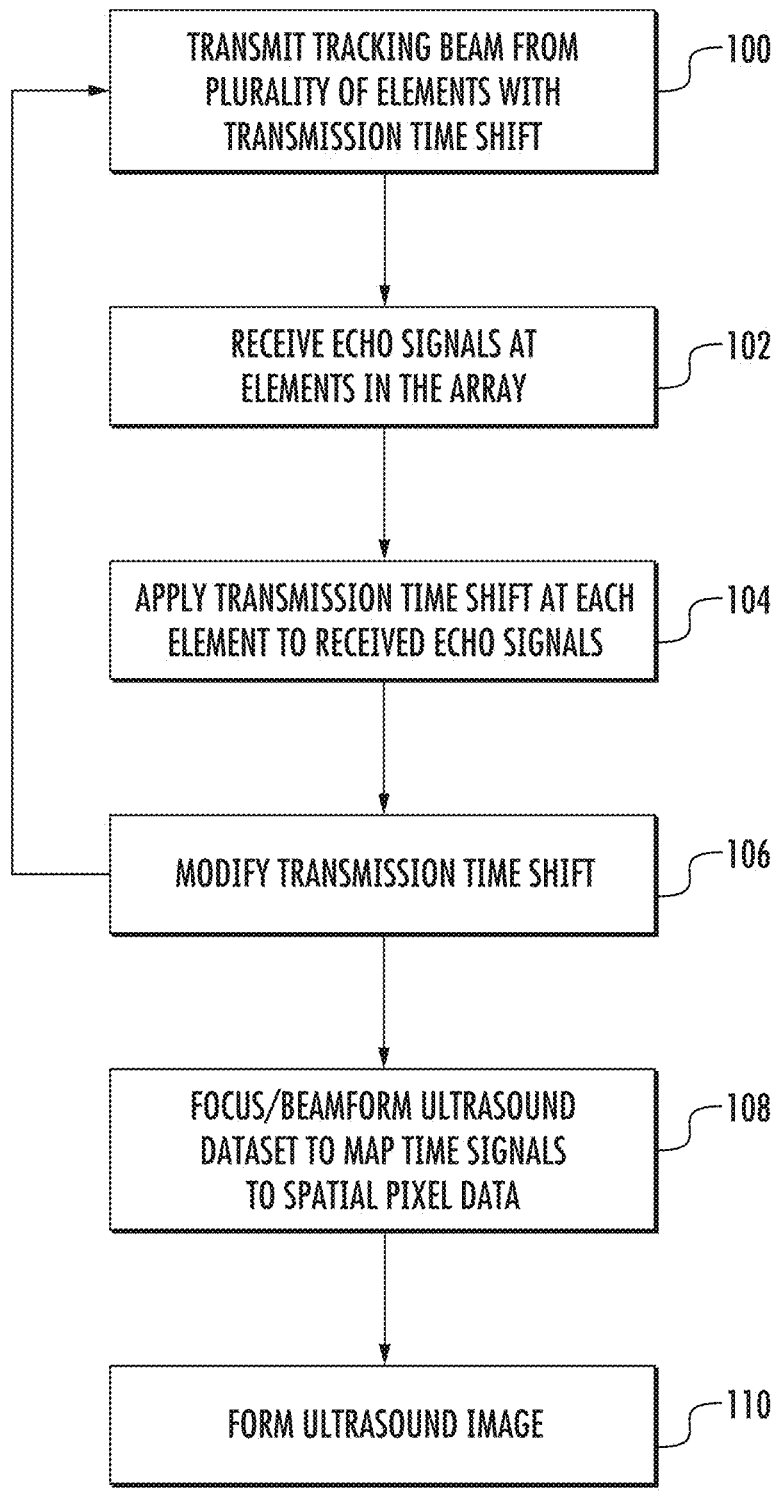
FIG. 2 is a flowchart of operations according to some embodiments.

As illustrated in FIG. 2, an ultrasound tracking beam is transmitted by instructions from the ultrasound data acquisition controller 22 with the ultrasound transducer array 40 (Block 100). At least a subset of the plurality of elements 42 of the transducer array 40 transmits a signal of the tracking beam with a respective transmission time shift. A plurality of echo signals is received at at least some of the subset of the plurality of elements 42, each element being responsive to the tracking pulse (Block 102). A transmission time shift of the respective elements transmitting the signal is applied to the echo signals received at corresponding ones of the plurality of elements 42 (Block 104). The transmission time shift is modified and the steps at Blocks 100-104 are repeated to form an ultrasound dataset (Block 106). The ultrasound dataset is focused and beamformed to map time signals of the ultrasound dataset and combine channel signals to provide spatial pixel data (Block 108), which is used to form an ultrasound image (Block 110).

Various time shifts may be used. In some embodiments, the respective transmission time shift of the elements forms a time shift encoding matrix, and the time shift encoding matrix may be formed of randomly generated time shift values. By "randomly" generated, it is meant that the time shift values may be predetermined, such as by a random number generator or lookup table of random values. In some embodiments, the random values may be between a given range of values.

In some embodiments, the time shift encoding matrix may be formed by focused, plane or diverging time delays.

In some embodiments, post-processing may be applied to the recovered source element domain of the ultrasound dataset.

In some embodiments, the transmission time shift is applied to edge elements of the array. That is, the transmission time shift is applied and/or modified as Blocks 100-104 are repeated at selected elements of the array along the perimeter of the array. Moreover, by "edge elements" it is meant that the selected edge elements may extend inward to the central portion of the array as long as some of the central array elements do not have a transmission time shift applied.

In some embodiments, the transmission time shift is applied to all of the elements in the array.

In some embodiments, the step of beamforming includes a delay and sum beamforming method across ultrasound element dimensions to form an image.

A non-limiting example focusing method according to the above steps is described below.

Method 1—Focusing

For purposes of the following discussion, the ultrasound array has elements located at positions $E_l$, where l indexes the L total elements. The transmit field response for excitation of each element is given by $u_l(t)$, where t is time.

The recorded set of radio frequency (RF) backscattered echoes $s_{mn}[t]$ is the sampled signal through time t and indexed by receiving element m, with M=L total receiving elements, and emission n, with N total transmit events. When each element is individually excited and the backscattered echoes are sampled on each receiving channel, L=M=N and the complete data set is acquired. The n dimension of the recorded data set smn[t] then has one-to-one correspondence with the set of transmit responses $u_l(t)$.

Figure 4A:
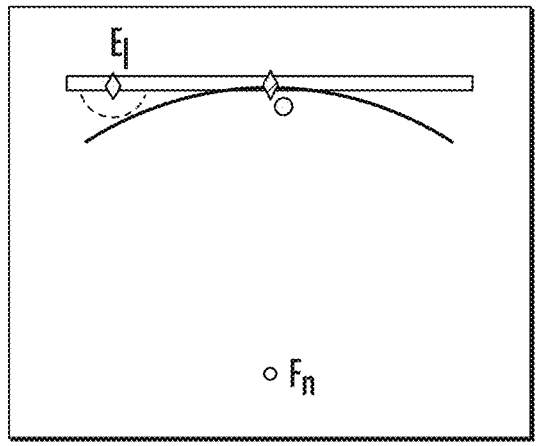
FIG. 4A is a schematic illustration illustrating a transmit event focused at point F that is referenced in time to the beam origin O, the last point on the array to emit the wave. The focused wavefront is made up of individual spherically divergent waves (dased) from the transmit element $E_I$ according to some embodiments.

The transmit focusing process is illustrated in FIG. 4A. Transmit focusing is performed by delaying the emissions from individual elements along the array $E_l$. The emissions are focused to the point $F_n$, where n indexes the N focal points of the scan sequence, each corresponding to a transmit beam from origin O. It is assumed in this notation that the focused wave crosses the beam origin at time t=0 relative to the recorded channel signal.

To find the total field response of the focused array $v_n(t)$, the response of each element $u_l(t)$ is delayed by $\tau_{ln}$ so that the individual element waves constructively interfere at Fn:

$$v_n(t) = \sum_{l=1}^{L} u_l(t - \tau_{ln}) \tag{1}$$

The appropriate delay is computed using the difference in assumed propagation path length between each element and the focus relative to the origin. The distance is scaled by the assumed speed of sound c:

$$\tau_{ln} = \frac{\|\overrightarrow{OF_n}\| - \|\overrightarrow{E_l F_n}\|}{c} \tag{2}$$

Figure 4B:
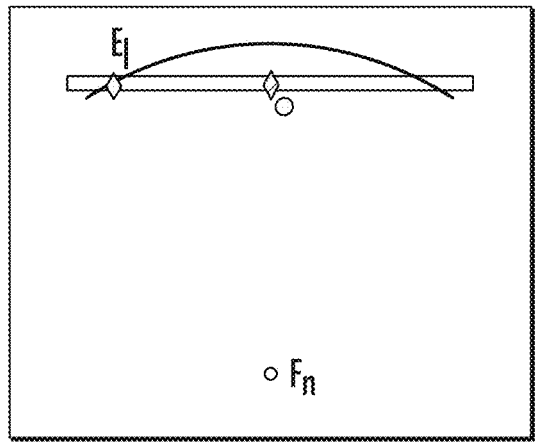
FIG. 4B is a schematic diagram illustrating the ultrasound wave in which the time is calculated at which the wave is emitted from the chosen transmit element $E_I$ for the transmit event m, which is prior to O according to some embodiments.

Focusing is performed by temporal interpolation of the recorded channel data based on assumed propagation time. Propagation from a selected element $E_l$ may begin at a different time than from the beam origin O. To correct for this, a time adjustment $t_{ln}$ must be calculated based on the transmit focal profile as shown in FIG. 4B:

$$t_{ln}^{adjust} = \tau_{ln} \tag{3}$$

Figure 4C:
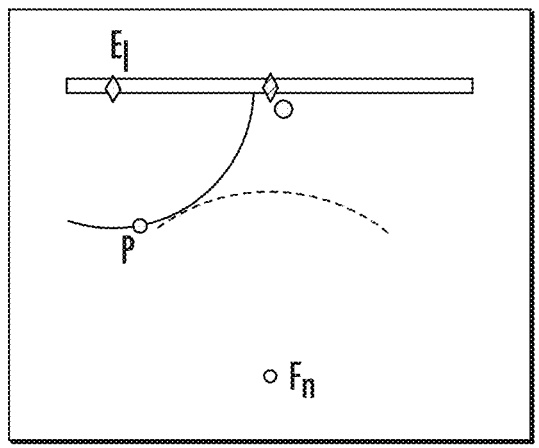
FIG. 4C is a schematic diagram illustrating the spherical propagation of the wave from $E_I$ that is followed to the point to be reconstructed P. The focused wave (dashed) is tangent to this spherical wavefront according to some embodiments.

For elements that transmitted before the transmission from the origin, as in the diagram, this value is negative and results in looking at earlier times in the recording signal. The second propagation path is shown in FIG. 4C, from $E_l$ to the point to be reconstructed P. Spherical propagation of the wave, as from a point source, is assumed. This forward propagation time is based on the radial distance between the element and point:

$$t_{lp}^{forward} = \frac{\|\overrightarrow{E_l P}\|}{c} \tag{4}$$

The isochronous curve for the contribution of $E_l$ is drawn as a solid arc in the diagram. At the time that this wave intersects the spatial point P, the geometric focused wave is at the position indicated by the dashed arc, spherically converging toward the focal point Fn and tangent to the contribution of $E_l$. The final propagation time $t_{lp}^{backward}$ that of the backscattered wave traveling from P to each receive element of the array Em (not pictured in the diagram):

$$t_{lp}^{backward} = \frac{\|\overrightarrow{PE_m}\|}{c} \tag{5}$$

Figure 4D:
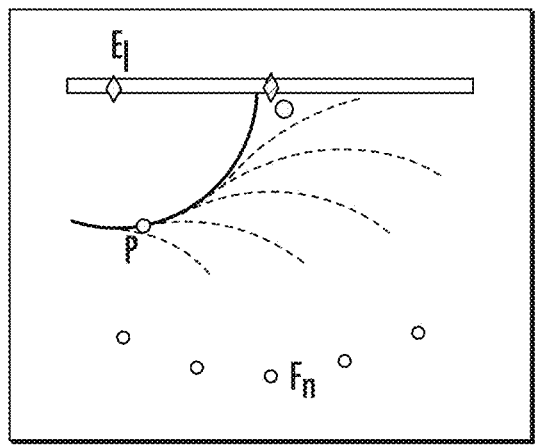
FIG. 4D is a schematic diagram illustrating that the process of FIGS. 4A-4C is repeated for various transmit focal points $F_n$, coherently reinforcing the spherical wave and incoherently suppressing the spatially-varying focused waves according to some embodiments.

FIG. 4D shows the synthesized transmit field after repeating the process of FIG. 4C for multiple transmit events with focal points Fn. The contribution of $E_l$ is coherently reinforced, while the geometric waves are incoherently suppressed at other spatial locations. The method depends on sufficient signal-to-noise ratio between these coherent and incoherent components. The focused data set $r_{lmp}$ indexed by source element, receive channel, and spatial point can be produced by interpolation using the three propagation times and summation over transmit events:

$$r_{lmp} = \sum_{n=1}^{N} s_{mn}\left[t = t_{ln}^{adjust} + t_{lp}^{forward} + t_{mp}^{backward}\right] \tag{6}$$

At this stage, any processing as a function of source element and/or receive channel can be performed as on the complete data set. The final beamformed RF data $r_p$ can then be produced by summation over the source element and receive channel dimensions:

$$r_p = \sum_{l=1}^{L} \sum_{m=1}^{M} r_{lmp} \tag{7}$$

Method 2—Decoding

Figure 3:
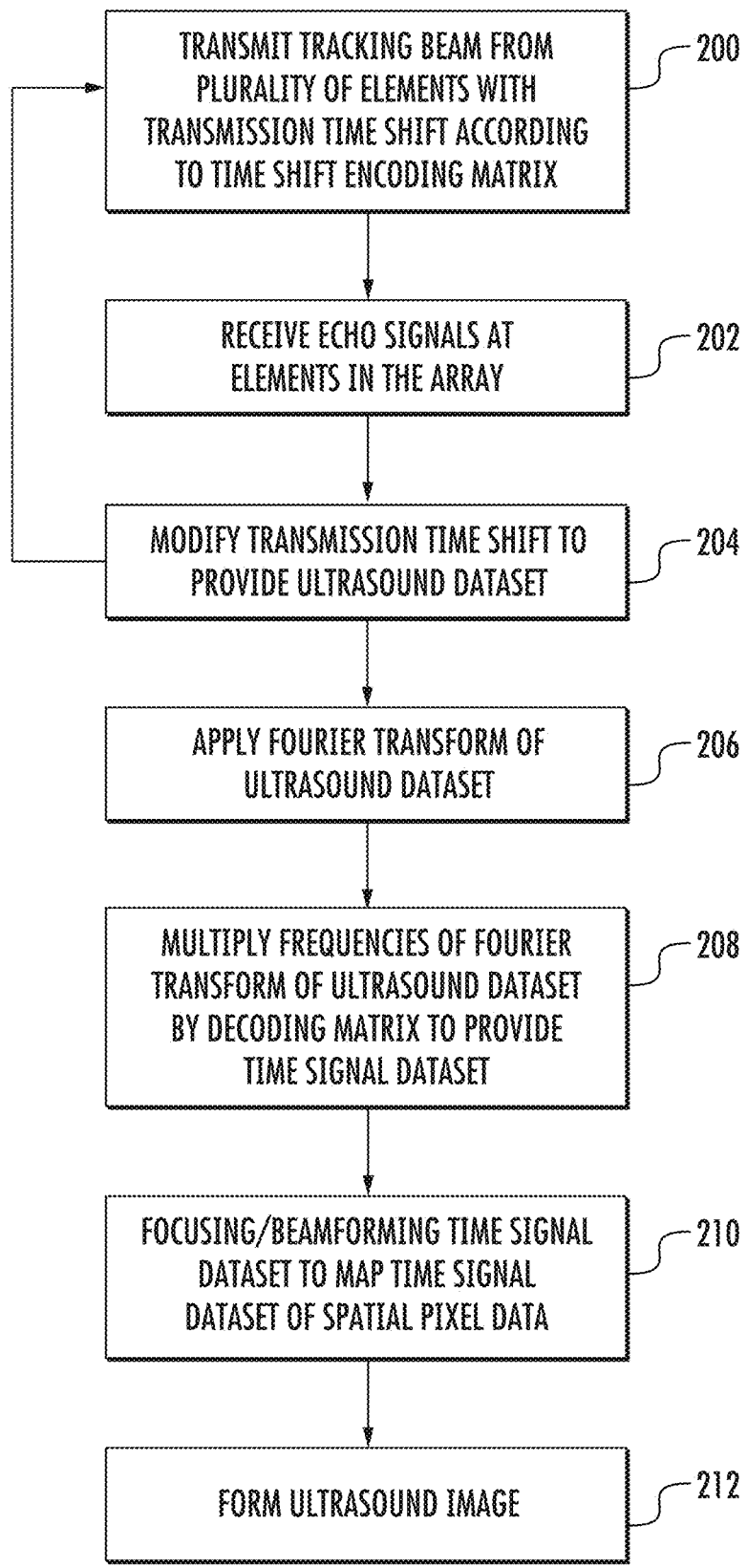
FIG. 3 is a flowchart of operations according to some embodiments.

As illustrated in FIG. 3, an ultrasound tracking beam is transmitted by instructions from the ultrasound data acquisition controller 22 with the ultrasound transducer array 40 with transmission time shifts according to a time shift encoding matrix (Block 200). Accordingly, at least a subset of the plurality of elements 42 of the transducer array 40 emits a signal of the tracking beam with a respective transmission time shift according to the time shift encoding matrix. A plurality of echo signals is received at at least some of the subset of the plurality of elements 42, responsive to the tracking pulse (Block 202). The transmission time shift is modified, and the steps at Blocks 200-202 are repeated to form an ultrasound dataset (Block 204). A Fourier transform is applied to the ultrasound data set (Block 206) and the frequencies of the Fourier transform of the ultrasound dataset are multiplied by a decoding matrix and an inverse Fourier transform is applied to provide a time signal dataset (Block 208). The decoding matrix is a conjugate transpose of the time shift encoding matrix. The ultrasound dataset is focused and beamformed to map time signals of the ultrasound dataset and combine channel signals to provide spatial pixel data (Block 210), which is used to form an ultrasound image (Block 212).

Various time shifts may be used. The time shift encoding matrix may be formed of randomly generated time shift values. In some embodiments, the time shift encoding matrix may be formed by focused, plane or diverging time delays.

In some embodiments, post-processing may be applied to the recovered source element domain of the ultrasound dataset.

In some embodiments, the transmission time shift is applied to edge elements of the array. That is, the transmission time shift is applied and/or modified as Blocks 200-202 are repeated at selected elements of the array along the perimeter of the array. In some embodiments, the transmission time shift is applied to all of the elements in the array.

In some embodiments, the step of beamforming includes a delay and sum beamforming method across ultrasound element dimensions to form an image.

It is noted that the order of various steps described herein may be modified as would be understood by one of ordinary skill in the art. For example, the focusing step of Blocks 108 and 210 in FIGS. 2-3 and as shown in FIG. 4B depends on the focal point and recovered element position, not on the point to be reconstructed. The linear steps (transmit delay adjustment, pixel-based focusing, and summation over transmit events) can therefore be reordered to perform pixel-based focusing after summation of the transmit events, which reduces the dimensionality of the data set.

The physical interpretation of this reordering is that the summation coherently reinforces the point source at the selected recovered element. The energy from all of the other sources are spatially incoherently mixed at this initial time, so the data are treated as if the selected element was the only active element. The emission from that element is then tracked as a spherically spreading wave as in conventional diverging wave beamforming while the energy from the other sources propagates through the field in various directions, making it temporally and spatially incoherent with the desired component.

Focusing the array on emission, as depicted in FIG. 4A can be viewed as a time-shift spatial coding of the transmit elements. For each emission, elements receive an encoding time shift of $\tau_{l,n}$ from equation (2) and are summed together to form the focused wave. This can be implemented in the time domain as time shifts as described above, but can also be implemented efficiently in the frequency domain where each time shift becomes a complex phase shift at angular frequency $\omega$. The coding matrix H contains one column for each emission, where rows represent the phase shift corresponding to each element:

$$H = \begin{bmatrix} e^{-j\omega\tau_{1,1}} & e^{-j\omega\tau_{1,2}} & \ldots & e^{-j\omega\tau_{1,N}} \\ e^{-j\omega\tau_{2,1}} & e^{-j\omega\tau_{2,2}} & \ldots & e^{-j\omega\tau_{2,N}} \\ \vdots & \vdots & \ddots & \vdots \\ e^{-j\omega\tau_{L,1}} & e^{-j\omega\tau_{L,2}} & \ldots & e^{-j\omega\tau_{L,N}} \end{bmatrix} \quad (8)$$

Given the Fourier transform of the backscattered response from individual elements $X=[X_1 X_2 ::: X_L]$, the Fourier transform of the recorded backscattered response from the focused emissions $Y=[Y_1 Y_2 ::: Y_N]$ is described by the linear system:

$$Y = XH \quad (9)$$

Applying the transmit delay adjustment as previously described requires applying the opposite phase shift $-\tau_{l,n}$ for the selected element to all transmit event data. This ensures that the desired individual element response has its phase exactly canceled while the other components retain varying phase shifts across the set of transmit events. To properly isolate the desired component, these residual phases must be distributed fairly uniformly between $[-\pi, \pi]$ such that they incoherently sum across transmit events. A matrix $H^+$ is defined where each column represents the recovery of a single source element and each row describes one focused emission. This matrix is simply the conjugate transpose $H^-$ of the coding matrix:

$$H^* = \begin{bmatrix} e^{j\omega\tau_{1,1}} & e^{j\omega\tau_{2,1}} & \ldots & e^{j\omega\tau_{L,1}} \\ e^{j\omega\tau_{1,2}} & e^{j\omega\tau_{2,2}} & \ldots & e^{j\omega\tau_{L,2}} \\ \vdots & \vdots & \ddots & \vdots \\ e^{j\omega\tau_{1,N}} & e^{j\omega\tau_{2,N}} & \ldots & e^{j\omega\tau_{L,N}} \end{bmatrix} \quad (10)$$

This matrix is applied to the recorded data to recover estimates of the individual element responses:

$$\hat{X} = YH^* = X(HH^*) \quad (11)$$

Figure 5A:
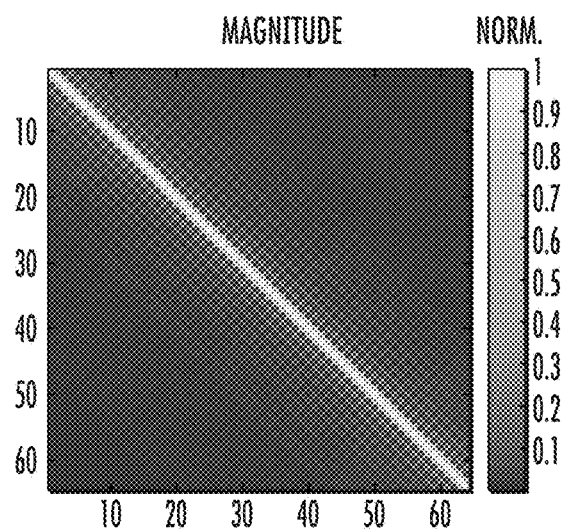
FIG. 5A is a diagram of the magnitude of H H$^+$ at $\omega=2\pi f_0$ for $f_o=3$ MHz for a sample phased array scan according to some embodiments.
Figure 5B:
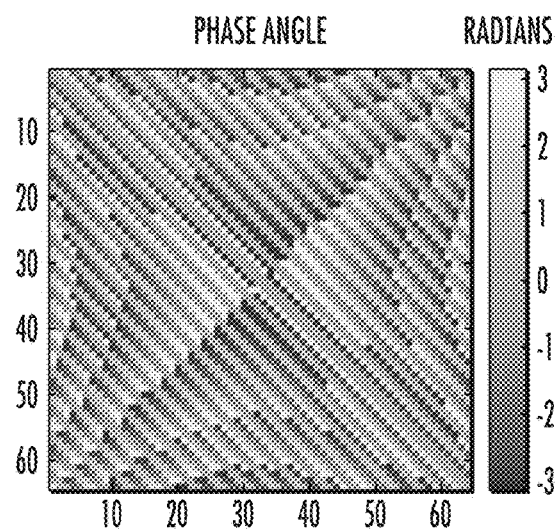
FIG. 5B is a diagram of the phase of H H$^+$ at $\omega=2\pi f_0$ for $f_o=3$ MHz for a sample phased array scan according to some embodiments.

The extent to which this estimate matches the original element responses is determined by the encoding/decoding term $(HH^+)$. If $H^+$ were the true pseudoinverse of H, the encoding/decoding would equal the identity matrix and ideally recover X Application of an appropriate pseudoinverse of H rather than using $H^-$ could improve the decoding. FIGS. 5A-5B show the mathematical result of encoding/decoding in magnitude and phase plots calculated at the center frequency. The parameters for this example were a 64 element array with $\lambda=2$ pitch with center frequency 3 MHz, focused at 4 cm and steered from $[-30; 30]$ degrees in 0.5 degree increments.

The resulting data set of the individual element responses is unfocused. Focusing is performed using standard diverging wave beamforming methods to produce the complete focused data set.

The methods described herein can be generalized to other array geometries such as a matrix array by modifying the positions $E_l$. Other choices of phase delays than the proposed spherically focused timings in equation (2) can be used as long as the selected steerings produce sufficient orthogonality over the scan sequence (such that $HH^+$ approximates an identity matrix). The same methods also apply to harmonic imaging, where the decoded signals may not directly correspond to physical element responses because the harmonic signal is generated during propagation.

In some embodiments, the methods described herein may be used to decode or defocus the received data. Existing synthetic aperture methods are based on the virtual source assumption, treating the focal point as a spherical point source and tracking the geometric wave toward and away from this point. The result of the assumption is that the data from the physical aperture is used directly near this focal point rather than forming a synthetic aperture. As described herein, some embodiments model the physical elements as sources, removing this restriction. Accordingly, the necessity for careful characterization of the transmit beam profile required by prior virtual source methods may be omitted.

Current spatial coding methods use a mathematically coded set of amplitudes (or 180 degree phase shifts to approximate amplitude inversions) to increase the number of elements fired during each transmit event. Viewed as a spatial decoding, in some embodiments, conventional focal delays (non-binary, arbitrarily selected) may be used as an encoding method. All elements may be used on every emission without requiring polarity inversion.

Conventional beamforming methods typically have limited signal-to-noise ratio at depth and a narrow depth of field around the fixed transmit focus. A traditional trade-off is to select a deep transmit focus to maximize penetration but sacrifice resolution closer to the array. These effects obscure clinically important targets by creating geometric distortions, increased off-axis scattering that overwrites hypoechoic targets, and temporally unstable noise. Commercial scanners already use some degree of synthetic transmit aperture beamforming and are progressing toward using flexible software beamforming rather than dedicated hardware. Some embodiments of the invention are directly translatable to these systems by modifying the software beamformer and would improve image quality compared to existing methods. The technique is broadly applicable to different scan sequences and clinical imaging targets. The proposed method can also be applied in parallel with conventional beamforming because both use the same input data set.

Embodiments according to the invention will now be described with respect to the following non-limiting examples.

Example 1

Data was acquired with the Verasonics research scanner processed offline. The Verasonics P4-2v phased array (3 MHz, 64 elements, 0.3 mm pitch) was used to acquire receive channel data of an ATS calibration phantom and in vivo human liver. In the phantom, a 60 degree span of beams sampled at 0.25 degrees was acquired using a transmit focus of 40 mm. In the liver, a 60 degree span of beams sampled at 0.5 degrees was acquired using a transmit focus of 50 mm. Each data set was processed with both conventional dynamic receive focusing and the proposed method. Resolution away from the transmit focus and signal-to-noise ratio at depth is improved in both cases.

Figure 6A:
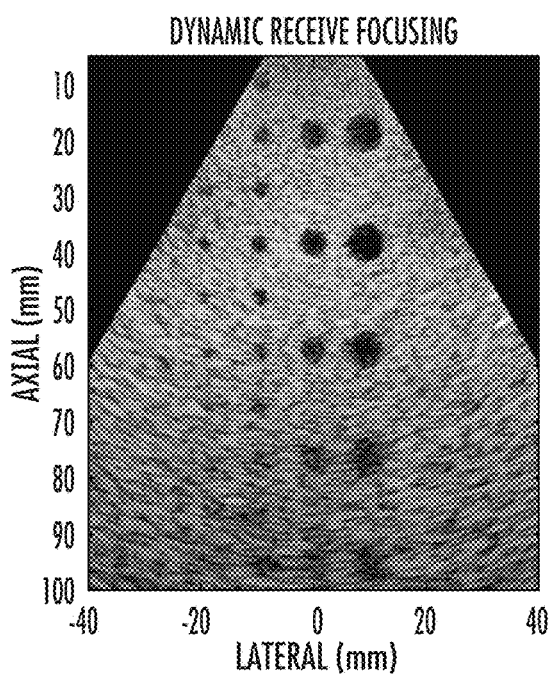
FIG. 6A is an image of an anechoic lesion phantom produced with conventional dynamic receive focusing.
Figure 6B:
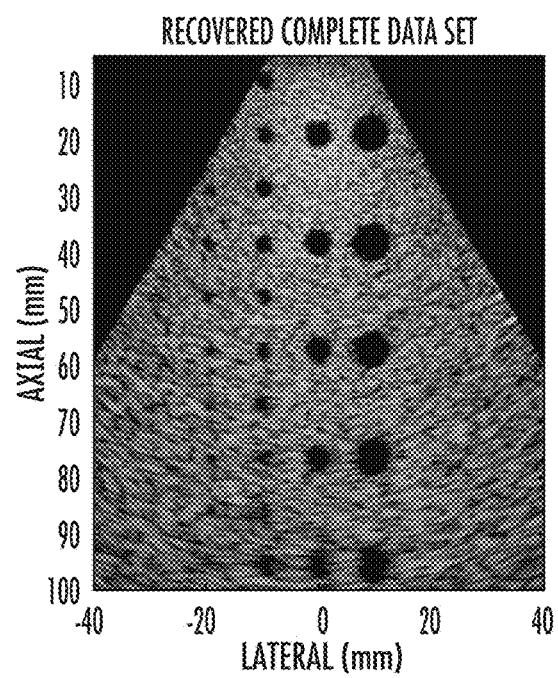
FIG. 6B is an image of an anechoic lesion phantom produced with recovery of the complete data set according to some embodiments.

The image of an anechoic lesion phantom produced with conventional dynamic receive focusing are shown in FIG. 6A, and an image of the phantom produced according to embodiments of the invention to provide recovery of the complete data set is shown in FIG. 6B. Both images were produced from the same recorded channel data set and are shown with 50 dB dynamic range. An image of a vasculature from an in vivo human liver produced with conventional dynamic receive focusing are shown in FIG. 7A, and an image of the liver produced according to embodiments of the invention to provide recovery of the complete data set is shown in FIG. 7B. Both images were produced with the same recorded channel data set.

Transmit depths of field and electronic signal-to noise ratio are improved by the recovery of the complete dataset in FIGS. 6B and 7B as compared with conventional dynamic receive focusing as shown in FIGS. 6A and 7A.

Example 2

A B-mode ultrasound image is conventionally formed by transmitting pulses from elements of an array transducer, phased relative to one another in order to steer and focus the ultrasound beam across a field of view. Alternatively, focused transmit beams can be produced using a transducer with a mechanical focusing mechanism (e.g. a lens). Backscattered echoes are collected on the receiving elements and are electronically focused at distances along the focal line to produce an A-line. For a 2-D example, the assumed total time of flight of the wave to each receive element is given by $$t(i) = t_{tx}(i) + t_{rx}(i) = \frac{\left\| \vec{P} - \vec{O} \right\| + \left\| \vec{X}(i) - \vec{P} \right\|}{c} \quad (12)$$

for imaging points $\vec{P}=(x_p, z_p)$ on the beam line, receive element locations $\vec{X}(i)=(x_i, 0)$ and beam origin $\vec{O}=(0, 0)$. Reconstructed A-lines from multiple transmit events are scan-converted onto a Cartesian grid if necessary for display. Parallel receive imaging adjusts the receive path length calculation for beams steered slightly off-axis to enable scans with sparser transmit beam spacing. Rather than assuming that the energy of the transmitted wave is restricted to the beam axis, synthetic aperture methods instead perform reconstruction of off-axis regions for each transmit beam. For a focused emission, a spherical approximation is made that a wave converges toward the focal point and diverges from that point as a spherical (or circular for 2-D) wave, often with a restricted opening angle in the beam direction (creating an "hourglass" shape). The total time of flight is therefore based on radial isochronous contours relative to the focal point, where any point located at the same radius is insonified by the transmitted pulse simultaneously. The modified focal equation for a focus at $\vec{F}=(x_f, z_f)$ and points ~P located throughout the hourglass shape is $$t(i) = \frac{\left\| \vec{F} - \vec{O} \right\| \pm \left\| \vec{P} - \vec{F} \right\| + \left\| \vec{X}(i) - \vec{P} \right\|}{c} \quad (13)$$

where the ±symbol is positive for points beyond the focus and negative for points between the transducer and focus.

Figure 8:
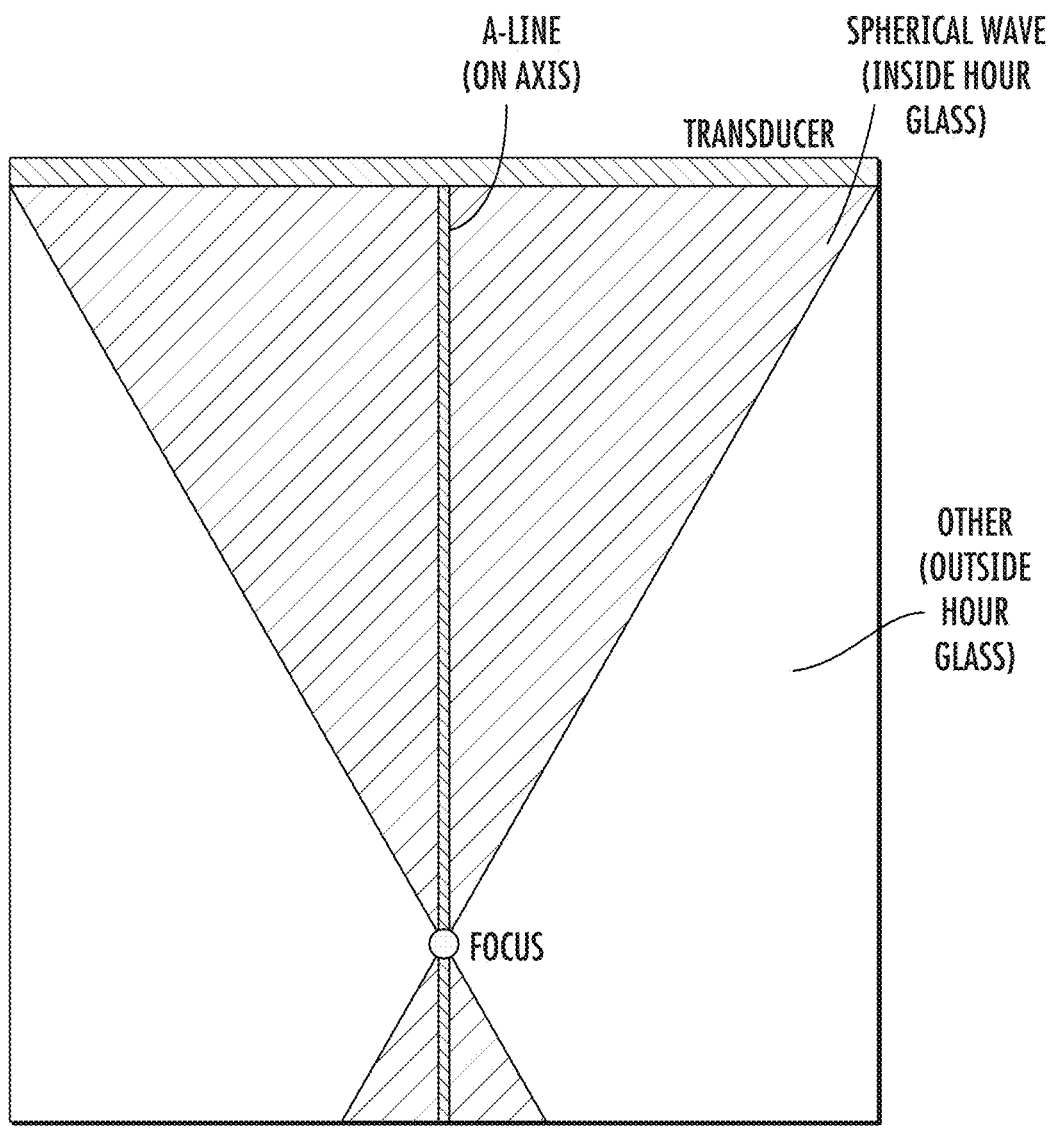
FIG. 8 is a diagram of regions of a focused transmit beam reconstructed by different focusing schemes. The on-axis response is traditionally used in dynamic receive beamforming while the region inside the hourglass may be used in focused virtual source synthetic aperture beamforming.

The resulting subimages from each transmit event are then coherently compounded to create a synthetic transmit aperture defined by the steering angles of the beams. However, the spherical approximation only holds for points within this opening angle along the beam direction, roughly converging to a point at the focus. For image points outside this region, such as those laterally offset from the focus, other approximations have been made to avoid gaps and discontinuities in the final image. The simplest option is to continue to use the spherical approximation for the transmitted wave, resulting in a sharp is continuity at the focal depth as the ±term switches signs. Parallel receive assumptions can be made, simply steering the receive focus without adjusting the transmit focus, resulting in discontinuities in the transition region between assumed wave shapes. The three regions that have been described for each transmit event—the on-axis beam, the region within the hourglass shape, and the region outside the hourglass shape—are illustrated in FIG. 8.

A discontinuity-free approach has been proposed that linearly interpolates between delays from the spherical approximation region. See M H Bae and M K Jeong, "A study of Synthetic-Aperture Imaging with Virtual Source Elements in B-Mode Ultrasound Imaging Systems," *IEEE Transactions on Ultrasonics, Ferroelectrics and Frequency Control*, vol. 47, no. 6, (November 2000). This method switches from a spherical wave assumption to a plane wave assumption at the boundaries of the hourglass region, matching the assumed wave arrival time to create a smooth function across the boundary. The modified time of flight equation in this case is based on the projection of the point-to-focus vector onto the beam direction and given by $$t(i) = \frac{\|\vec{F} - \vec{O}\| \pm (\vec{P} - \vec{F}) \frac{\vec{F} - \vec{O}}{\|\vec{F} - \vec{O}\|} + \|\vec{X}(i) - \vec{P}\|}{c} \quad (14)$$

for points outside the hourglass with θ representing half the opening angle of the hourglass (i.e. the angle between the focal direction and line connecting the edge of the array to the focus). Equation 13 is used for points within the hourglass. The projection operator term maps imaging points onto radii along the hourglass shape, ensuring continuity in the time of flight function between the two regions and across the focal depth. However, this method disregards the physically propagating transmit wave in favor of artifact suppression. Some embodiments of the current invention are similarly motivated by creating discontinuity-free images, but are based on the actual propagation time of the components of the transmitted wave. Outside the hourglass region, some embodiments predict that the incident pressure wave consists of two pulses, which correspond to the tails of the conventional point spread function. Inside the hourglass region, some embodiments predict the existence of these two pulses and a larger amplitude pulse that matches the spherical approximation commonly made. The two pulses obey the modified time of flight equations $$t_A(i) = \frac{\|\vec{P} - \vec{X}(A)\| - (\|\vec{F} - \vec{X}(A)\| - \|\vec{F} - \vec{O}\|) + \|\vec{X}(i) - \vec{P}\|}{c} \quad (15)$$

$$t_B(i) = \frac{\|\vec{P} - \vec{X}(B)\| - (\|\vec{F} - \vec{X}(B)\| - \|\vec{F} - \vec{O}\|) + \|\vec{X}(i) - \vec{P}\|}{c} \quad (16)$$

for $\vec{X}(A)$ and $\vec{X}(B)$ corresponding to the edges of the active aperture. The approximation made here is that the edges of the aperture produce effectively a diverging wave, offset at the zero time (the time the main pulse is launched) based on the focal geometry. The spherical wave should not be present in the region outside the hourglass, making the combined form of Equations 13 and 14 acceptable for all regions since it is discontinuity-free. The transit times for all three components converge at the focus, as expected for the focused wavefront.

Figure 9:
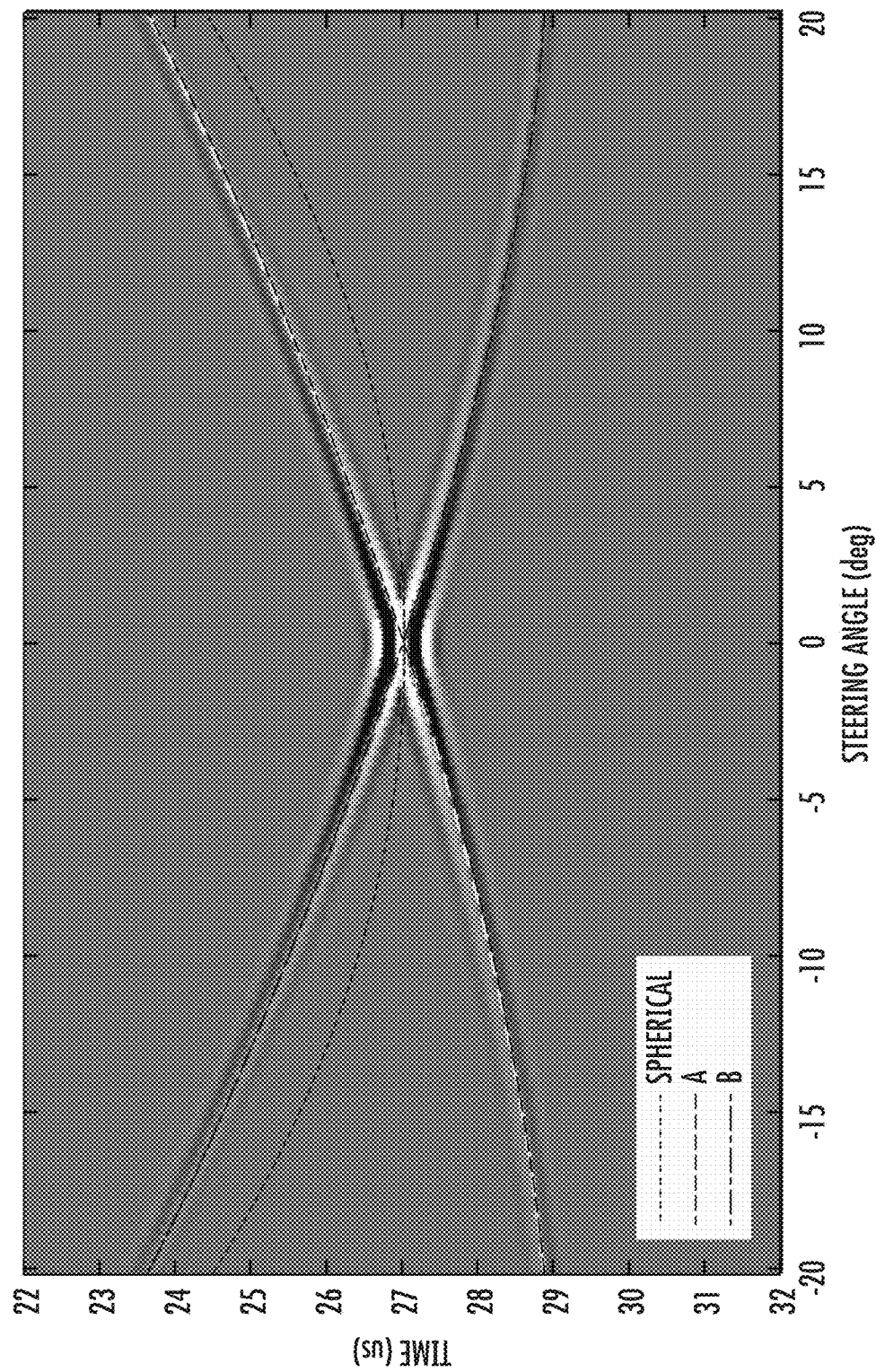
FIG. 9 is a simulated transmit pressure response at a single field point for different focused transmit beam steering angles according to some embodiments. For each angle the different timing equations are plotted. Only the interpolated version of the spherical timing equation is used because the observation point is at the focal depth and therefore never made inside the hourglass region where the spherical approximation would be valid.
Figure 10:
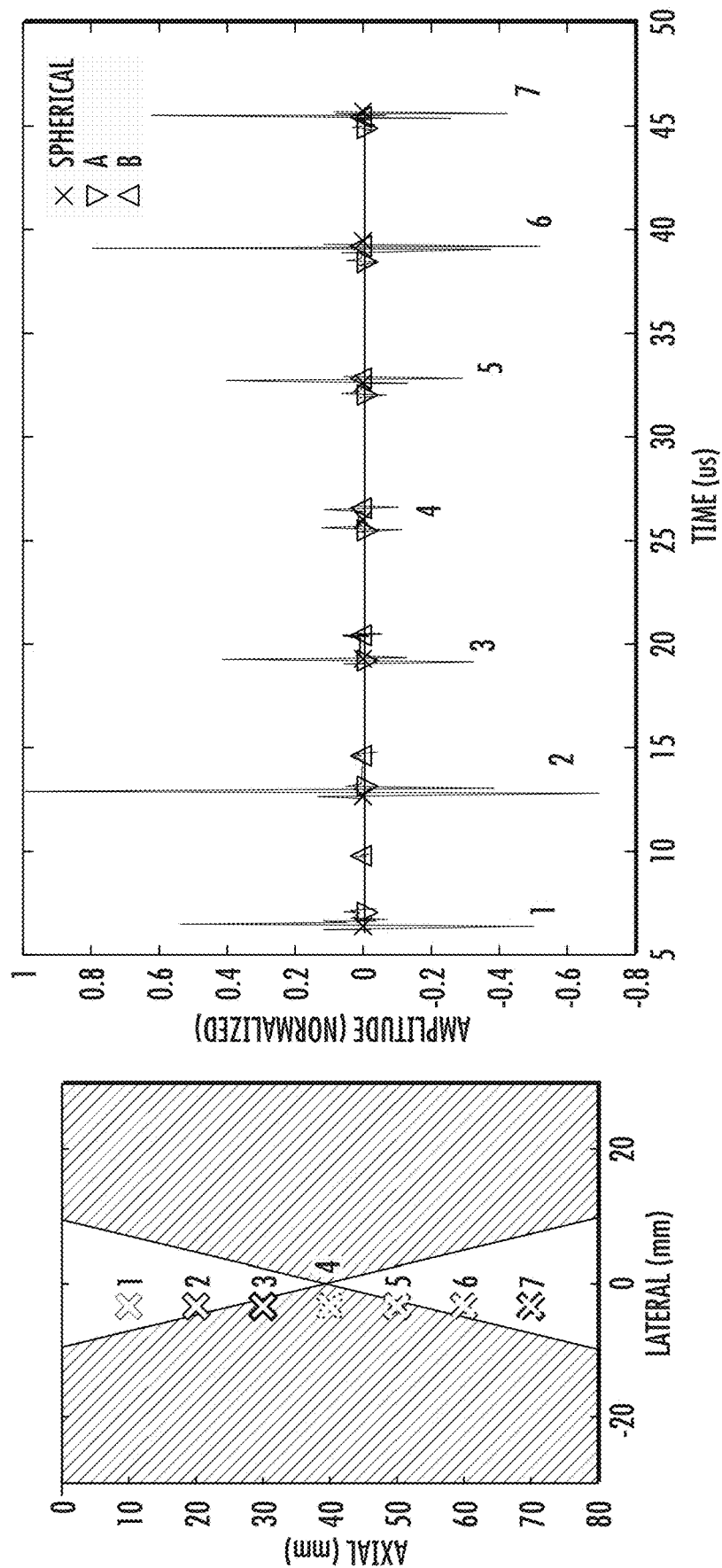
FIG. 10 is a diagram of simulated transmit pulses 1-7 as seen at different field points and matched to the delays calculated herein according to some embodiments.
Figure 11:
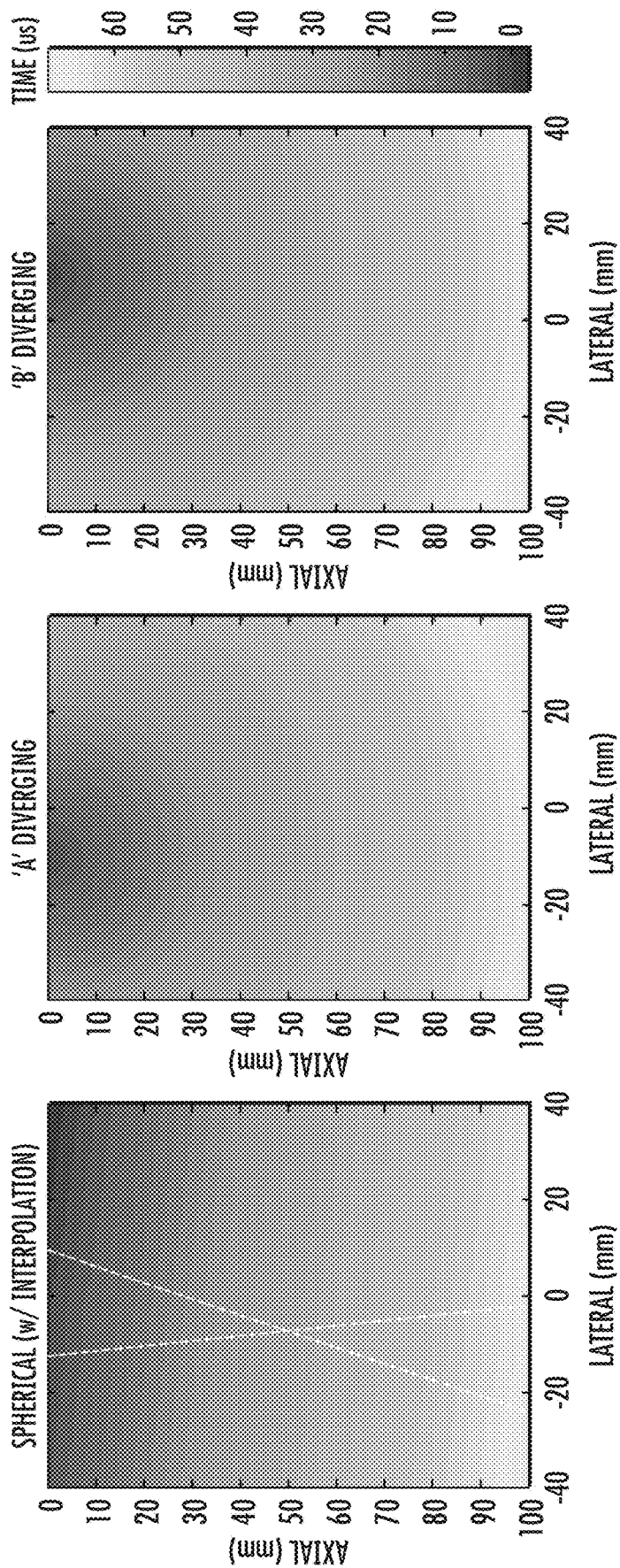
FIGS. 11A-11C is a graph of delays calculated for all field points for constituent parts of a steered transmit pulse according to some embodiments.

To demonstrate these principles, the predicted wave arrival times at a point in the field are shown for varying transmit steering angle along with the simulated ultrasound pulses in FIG. 9. Similarly, FIG. 10 shows simulated transmit pulses at different field points for a single transmit beam matched to the predicted arrival times. FIG. 11 ilustrates sample transmit wave arrival time maps used in beamforming for a steered transmit beam for each of the desired components.

Unlike conventional synthetic aperture beamforming techniques where a single subimage is produced from each transmit event, the proposed methods produce multiple subimages in parallel using the same set of input data using delays as in FIGS. 11A-11C or Equation 12. A single imaging sequence creates a final focused data set with dimensions (image points, pixels or voxels x receive channel x transmit event x pulse component). In some embodiments, compounding with the final dimension are possible, while conventional techniques address compounding schemes over receive channels and transmit events. Coherent or incoherent compounding of the pulse components can be performed before or after the conventional compounding over the other dimensions of the data set. It is also possible to choose a subset of the pulse components for compounding, or different subsets for different image points, receive channels or transmit events. The component pulses represent unique spatial frequency information and the received echoes can be focused such that pulses other than the component of interest become incoherent.

Additional pulse components beyond those described here are expected to arise in some imaging scenarios. The use of multiple subapertures or a matrix transducer would produce extra transmit pulse components that could be accounted for using extension of the geometrical descriptions provided above. The use of multiple transmit beams (varying steering angle or focal depth), spatially modulated transmit configurations or multiple transmit pulses would similarly produce additional components. The relative contribution of different pulse components may be adjusted using transmit array apodization, including complete suppression of the main spherical pulse or the edge pulses. For scenarios such as harmonic imaging, the backscattered echoes may not be directly proportional to the transmit pulse component intensities.

In some embodiments, it may be beneficial to spatially restrict the reconstructed data for some or all components to reduce the impact of signal with low electronic signal-to-noise ratio. This restriction can be done based on the assumed, simulated or calibrated geometry of the transmit beam profile or adaptively based on other data quality metrics.

Figure 12:
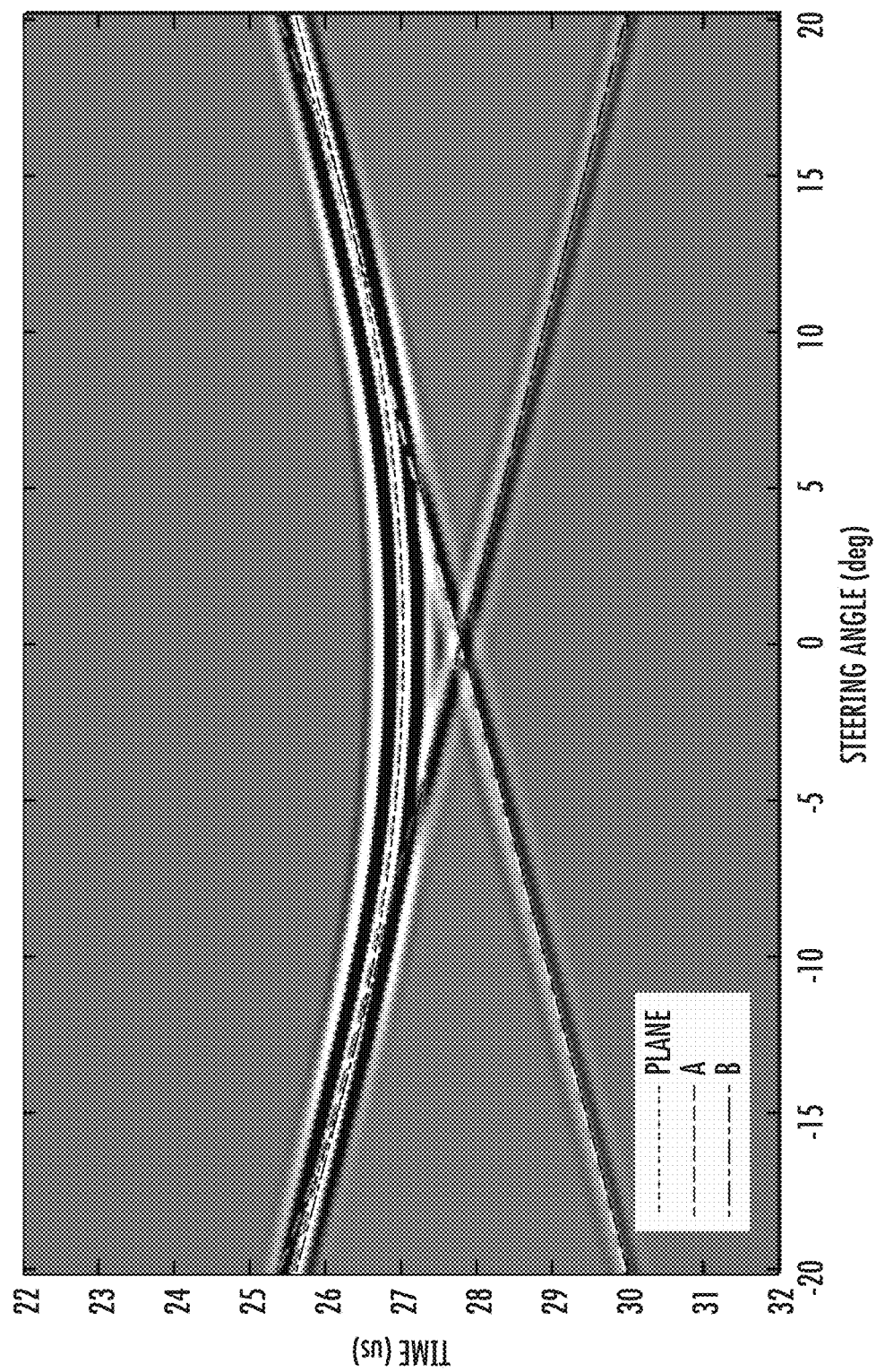
FIG. 12 is a diagram of a simulated transmit pressure response at a single field point for different plane wave transmit beam steering angles according to some embodiments. For each angle, the different timing equations are plotted. For large steering angles, either pulse A or pulse B coincides with the main plane wave pulse.

Embodiments according to the invention extend to other transmit configurations as well, including defocused or unfocused (plane) waves. Unlike focused transmit beams, these beams are typically used to reconstruct a wide field of view from each transmit event and multiple transmit events may be coherently compounded. While the main pulse in a focused transmit is confined to small angles from the beam axis, the main pulse of a defocused or unfocused wave is present at a larger range of angles. The edge components discussed previously coexist and may overlap with the main pulse but can still be used for intra-beam compounding. In current imaging implementations, these components are often considered "trailing clutter" and intentionally suppressed using transmit apodization. As an example, the modified time of flight equations for a plane wave with focal direction $\vec{F} = (\sin(\theta), \cos(\theta))$ are t(i)=

$$t(i) = \frac{(\vec{P} - \vec{O}) \cdot \vec{F} + \|\vec{X}(i) - \vec{P}\|}{c} \quad (17)$$

$$t_A(i) = \frac{\|\vec{P} - \vec{X}(A)\| - \|\vec{O} - \vec{X}(A)\| \sin(\theta) + \|\vec{X}(i) - \vec{P}\|}{c} \quad (18)$$

$$t_B(i) = \frac{\|\vec{P} - \vec{X}(A)\| - \|\vec{O} - \vec{X}(B)\| \sin(\theta) + \|\vec{X}(i) - \vec{P}\|}{c} \quad (19)$$

and the results are superimposed onto simulated pressure responses in FIG. 12.

Some embodiments according to the present invention may be distinct from previous work in that each focused transmit pulse is treated as multiple incident waves with differing spatial frequency information for targets in the field of view that can be compounded together irrespective of other transmit events. These methods do not preclude the use of multiple transmit events together for other compounding schemes as well. These methods do not require artificially restricting the active transmit or receive aperture to produce decorrelated subimages, and instead may rely on spatially varying components produced during the conventional focused transmit event.

The speckle artifact, with size on the order of the system resolution, is often a barrier to clinical diagnosis. The proposed methods would allow for speckle reduction or resolution improvement without reducing acquisition rate, limiting active aperture extent or performing costly adaptive post-processing. These methods are compatible with many existing technologies for image improvement, including pulse sequencing, receive beamforming and image post-processing. The technique may be well-suited to parallel processing architectures and software beamforming, both of which are increasingly common. The utility of the techniques is not limited to diagnostic ultrasound imaging and could be expand into other fields (e.g. contrast imaging, motion tracking) and modalities (e.g. radar, sonar).

This invention has been tested experimentally using data collected from a research scanner and processed offline. The Verasonics P4-2v phased array (3 MHz, 64 elements, 0.3 mm pitch) and the Verasonics Vantage scanner (Verasonics, Inc.) was used to acquire receive channel data of liver and liver vasculature from a volunteer. 129 focused emissions were performed over a span of 60 degrees and unfocused receive channel data was received for each. The data was processed in parallel in the following ways: conventional dynamic receive focusing, focused virtual source synthetic aperture focusing with interpolation, and focusing for the beam component from each edge of the array (as described above). Subimages were formed from each parallel data set before compounding, resulting in two images representing the main focused pulse (dynamic receive and synthetic aperture) and two images of other components, each representing one edge of the transmit aperture.

FIGS. 13A-13F illustrate the results of incoherent compounding of these subimages in varying proportions and the measured contrast-to-noise ratio from each image. It is likely that performance will vary as a function of axial distance from the focus and that a depth-dependent mixing of the components may be needed to optimize overall image quality. Similarly, performance can be expected to vary with electronic signal-to-noise ratio and could be adaptively compensated for.

The foregoing is illustrative of the present invention and is not to be construed as limiting thereof. Although a few example embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A method for ultrasound imaging a target region with an ultrasound system having an ultrasound transducer array with a plurality of ultrasound elements thereon, the method comprising:
  (a) transmitting an ultrasound tracking beam from at least a subset of the plurality of ultrasound elements of the ultrasound transducer array to the target region, each of the subset of the plurality of ultrasound elements comprising a plurality of emitting ultrasound elements that emit a signal of the ultrasound tracking beam with a respective transmission time shift;
  (b) receiving a plurality of echo signals at at least some of the subset of the plurality of ultrasound elements of the ultrasound transducer array, each of the plurality of echo signals being responsive to the ultrasound tracking beam;
  (c) applying the respective transmission time shift to at least some of the subset of the respective plurality of emitting ultrasound elements to the plurality of echo signals received at corresponding ones of the plurality of ultrasound elements;
  (d) modifying the respective transmission time shift and repeating steps (a)-(c) to provide an ultrasound dataset representing echo signals corresponding to a recovered source element domain for at least some of the subset of the plurality of emitting ultrasound elements of the ultrasound transducer array;
  (e) focusing and beamforming the ultrasound dataset to map time signals of the ultrasound dataset and combining channel signals to provide spatial pixel data, wherein a focused data set is generated by temporal interpolation of the channel signals; and
  (f) forming an ultrasound image from the spatial pixel data.

2. The method of claim 1, wherein the respective transmission time shift of each of the plurality of emitting ultrasound elements forms a time shift encoding matrix.

3. The method of claim 2, wherein the time shift encoding matrix comprises randomly generated time shift values.

4. The method of claim 2, wherein the time shift encoding matrix comprises focused, plane or diverging time delays.

5. The method of claim 1, the method further comprising applying post-processing on the recovered source element domain of the ultrasound dataset.

6. The method of claim 1, wherein the at least some of the subset of the respective plurality of emitting ultrasound elements comprise edge elements of the ultrasound transducer array.

7. The method of claim 1, wherein the at least some of the subset of the respective plurality of emitting ultrasound elements comprises all of the subset of the respective plurality of ultrasound elements.

8. The method of claim 1, wherein the step of beamforming comprises a delay and sum beamforming method across ultrasound element dimensions to form the ultrasound image.

9. A method for ultrasound imaging a target region with an ultrasound system having an ultrasound transducer array with a plurality of ultrasound elements thereon, the method comprising:
  (a) transmitting an ultrasound tracking beam from at least a subset of the plurality of ultrasound elements of the ultrasound transducer array to the target region, each of the subset of the plurality of ultrasound elements comprising a plurality of emitting ultrasound elements that emit a signal of the ultrasound tracking beam with a respective transmission time shift, wherein the respective transmission time shifts of each of the plurality of emitting ultrasound elements comprise a time shift encoding matrix;

(b) receiving a plurality of echo signals at at least some of the subset of the plurality of ultrasound elements of the ultrasound transducer array, each of the plurality of echo signals being responsive to the ultrasound tracking beam;

(c) modifying the respective transmission time shifts of each of the plurality of emitting ultrasound elements and repeating steps (a)-(b) to provide an ultrasound dataset;

(d) applying a Fourier transform to the ultrasound dataset;

(e) multiplying frequencies of the Fourier transform of the ultrasound dataset by a decoding matrix, the decoding matrix comprising a conjugate transpose of a Fourier domain representation of the time shift encoding matrix, to provide an ultrasound data set corresponding to a recovered source element domain for at least some of the subset of the plurality of emitting ultrasound elements of the ultrasound transducer array to recover estimates of individual ultrasound element signals;

(f) applying an inverse Fourier transform to the estimates of individual ultrasound element signals to provide a time signal dataset;

(g) focusing and beamforming the ultrasound dataset to map time signals of the ultrasound dataset and combining channel signals to provide spatial pixel data; and (h) forming an ultrasound image from the spatial pixel data.

10. The method of claim 9, wherein the time shift encoding matrix comprises randomly generated time shift values.

11. The method of claim 9, wherein the time shift encoding matrix comprises focused, plane or diverging time delays.

12. The method of claim 9, wherein the at least some of the subset of the respective plurality of emitting ultrasound elements comprise edge elements of the ultrasound transducer array.

13. The method of claim 9, wherein the at least some of the subset of the respective plurality of emitting ultrasound elements comprises all of the subset of the respective plurality of ultrasound elements.

14. The method of claim 9, wherein the step of focusing the ultrasound dataset to map the time signals of the ultrasound dataset to provide the spatial pixel data comprises complete dataset focusing.

15. The method of claim 9, wherein the step of beamforming comprises a delay and sum beamforming method across ultrasound element dimensions to form the ultrasound image.

16. A system for ultrasound imaging a target region, the system comprising:

an ultrasound transducer array with a plurality of ultrasound elements thereon; and a controller configured to (a) transmit an ultrasound tracking beam from at least a subset of the plurality of ultrasound elements of the ultrasound transducer array to the target region, each of the subset of the plurality of ultrasound elements comprising a plurality of emitting ultrasound elements that emit a signal of the ultrasound tracking beam with a respective transmission time shift; (b) receive a plurality of echo signals at at least some of the subset of the plurality of ultrasound elements of the ultrasound transducer array, each of the plurality of echo signals being responsive to the ultrasound tracking beam; (c) apply the respective transmission time shift to at least some of the subset of the respective plurality of emitting ultrasound elements to the plurality of echo signals received at corresponding ones of the plurality of ultrasound elements; (d) modify the respective transmission time shift and repeat steps (a)-(c) to provide an ultrasound dataset representing echo signals corresponding to a recovered source element domain for at least some of the subset of the plurality of emitting ultrasound elements of the ultrasound transducer array; (e) focus and beamform the ultrasound dataset to map time signals of the ultrasound dataset and combine channel signals to provide spatial pixel data, wherein a focused data set is generated by temporal interpolation of the channel signals; and (f) form an ultrasound image from the spatial pixel data.

17. The system of claim 16, wherein the respective transmission time shift of each of the plurality of emitting ultrasound elements forms a time shift encoding matrix.

18. The system of claim 17, wherein the time shift encoding matrix comprises randomly generated time shift values.

19. The system of claim 17, wherein the time shift encoding matrix comprises focused, plane or diverging time delays.

20. The system of claim 16, the controller further configured to apply post-processing on the recovered source element domain of the ultrasound dataset.

21. The system of claim 16, wherein the at least some of the subset of the respective plurality of emitting ultrasound elements comprise edge elements of the ultrasound transducer array.

22. The system of claim 16, wherein the at least some of the subset of the respective plurality of emitting ultrasound elements comprises all of the subset of the respective plurality of ultrasound elements.

23. The system of claim 16, wherein the step of beamforming comprises a delay and sum beamforming method across ultrasound element dimensions to form the ultrasound image.

24. A system for ultrasound imaging a target region, the system comprising:

an ultrasound transducer array with a plurality of ultrasound elements thereon; and a controller configured to (a) transmit an ultrasound tracking beam from at least a subset of the plurality of ultrasound elements of the ultrasound transducer array to the target region, each of the subset of the plurality of ultrasound elements comprising a plurality of emitting ultrasound elements that emit a signal of the ultrasound tracking beam with a respective transmission time shift, wherein the respective transmission time shifts of each of the plurality of emitting ultrasound elements comprise a time shift encoding matrix; (b) receive a plurality of echo signals at at least some of the subset of the plurality of ultrasound elements of the ultrasound transducer array, each of the plurality of echo signals being responsive to the ultrasound tracking beam; (c) modify the respective transmission time shifts of each of the plurality of emitting ultrasound elements and repeat steps (a)-(b) to provide an ultrasound dataset; (d) apply a Fourier transform to the ultrasound dataset; (e) multiply frequencies of the Fourier transform of the ultrasound dataset by a decoding matrix, the decoding matrix comprising a conjugate transpose of a Fourier domain representation of the time shift encoding matrix, to provide an ultrasound data set corresponding to a recovered source element domain for at least some of the plurality of emitting ultrasound elements of the ultrasound transducer array to recover estimates of individual ultrasound element signals; (f) apply an inverse Fourier transform to the estimates of individual ultrasound element signals to provide a time signal dataset; (g) focus and beamform the ultrasound dataset to map time signals of the ultrasound dataset and combine channel signals to provide spatial pixel data; and (h) form an ultrasound image from the spatial pixel data.

25. The system of claim 24, wherein the time shift encoding matrix comprises randomly generated time shift values.

26. The system of claim 24, wherein the time shift encoding matrix comprises focused, plane or diverging time delays.

27. The system of claim 24, wherein the at least some of the subset of the respective plurality of emitting ultrasound elements comprise edge elements of the ultrasound transducer array.

28. The system of claim 24, wherein the at least some of the subset of the respective plurality of emitting ultrasound elements comprises all of the subset of the respective plurality of ultrasound elements.

29. The system of claim 24, wherein the step of focusing the ultrasound dataset to map the time signals of the ultrasound dataset to provide the spatial pixel data comprises complete dataset focusing.

30. The system of claim 24, wherein the step of beamforming comprises a delay and sum beamforming method across ultrasound element dimensions to form the ultrasound image.

* * * * *